(12) United States Patent
Costa et al.

(10) Patent No.: US 10,119,109 B2
(45) Date of Patent: Nov. 6, 2018

(54) AUTOMATED, MULTIFUNCTIONAL, ENGINEERED CARDIAC TISSUE CULTURE AND TESTING BIOREACTOR SYSTEM

(71) Applicant: Icahn School of Medicine at Mount Sinai, New York, NY (US)

(72) Inventors: Kevin D. Costa, New York, NY (US); Peter Backeris, Union City, NJ (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/504,570

(22) PCT Filed: Aug. 25, 2015

(86) PCT No.: PCT/US2015/046635
§ 371 (c)(1),
(2) Date: Feb. 16, 2017

(87) PCT Pub. No.: WO2016/036532
PCT Pub. Date: Mar. 10, 2016

(65) Prior Publication Data
US 2017/0260488 A1    Sep. 14, 2017

Related U.S. Application Data

(60) Provisional application No. 62/046,569, filed on Sep. 5, 2014.

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/12* (2013.01); *C12M 23/22* (2013.01); *C12M 23/38* (2013.01);
(Continued)

(58) Field of Classification Search
CPC ...... C12M 21/08; C12M 41/48; C12M 23/12; C12M 23/22; C12M 23/38; C12M 23/50;
(Continued)

(56) References Cited

U.S. PATENT DOCUMENTS

2006/0239981 A1    10/2006    Yoo et al.
2007/0281349 A1    12/2007    Jaczynski
(Continued)

FOREIGN PATENT DOCUMENTS

WO    WO 2001/63248    8/2001
WO    WO 2014/085933    6/2014

*Primary Examiner* — Gautam Prakash
*Assistant Examiner* — Lydia Edwards
(74) *Attorney, Agent, or Firm* — Leason Ellis LLP

(57) ABSTRACT

An improved tissue engineering bioreactor and testing platform has been designed that integrates multiple testing and stimulation capabilities. The system allows for growth of multiple tissue strips in parallel with mechanical and electrical stimulation, media perfusion, and the automated monitoring of contractile force and extracellular electrical activity. The system is designed to be low-cost and scalable, to provide for high-content, biofidelic, non-destructive testing of engineered muscle tissue performance that is conventionally measured using muscle-bath systems.

18 Claims, 10 Drawing Sheets

(51) Int. Cl.
*C12M 1/42* (2006.01)
*C12M 1/34* (2006.01)
*C12M 1/36* (2006.01)
*C12M 1/32* (2006.01)

(52) U.S. Cl.
CPC ............ *C12M 23/50* (2013.01); *C12M 31/10* (2013.01); *C12M 35/02* (2013.01); *C12M 41/46* (2013.01); *C12M 41/48* (2013.01)

(58) Field of Classification Search
CPC ...... C12M 31/10; C12M 35/02; C12M 41/46; C12M 35/04
See application file for complete search history.

(56) References Cited

U.S. PATENT DOCUMENTS

| | | |
|---|---|---|
| 2009/0088680 A1 | 4/2009 | Aravanis et al. |
| 2009/0105574 A1 | 4/2009 | Young |
| 2009/0187258 A1 | 7/2009 | Ip et al. |
| 2010/0041972 A1 | 2/2010 | Mason |
| 2012/0178187 A1 | 7/2012 | Radtkey et al. |

AUTOMATED, MULTIFUNCTIONAL, ENGINEERED CARDIAC TISSUE CULTURE AND TESTING BIOREACTOR SYSTEM

CROSS-REFERENCE TO RELATED APPLICATION

This patent application is a U.S. National Phase Application under 35 U.S.C. § 371 of International Patent Application No. PCT/US2015/046635, filed Aug. 25, 2015, which is based on and claims priority to U.S. Provisional Patent Application Ser. No. 62/046,569, filed on Sep. 5, 2014, the entire contents of which is incorporated by reference herein as if expressly set forth in its respective entirety.

GOVERNMENT SUPPORT

This invention was made with government support under UL RR029887 awarded by NIH. The government has certain rights in the invention.

TECHNICAL FIELD

The present invention is directed to a bioreactor system for growing tissue (e.g., a plurality of cardiac tissue strips) under regulated electrical and mechanical stimulation and more specifically, to an improved bioreactor system that integrates measurement and control functionality into a tissue culture system to allow for automatic, real-time measurements to be taken without the need to interact with the tissue.

BACKGROUND

Much work has been done in recent years to develop 3-dimensional (3D) engineered cardiac tissues from multiple sources, primarily from isolated rat cardiomyocytes and human embryonic stem cell-derived cardiac cells, and now induced-pluripotent stem cell sources. These engineered tissues have been generated in a number of forms for a variety of purposes such as developing a patch for damaged heart tissue in patients with myocardial infarction (MI), as well as for serving as an in-vitro testing platform for screening potential therapeutic agents, testing for toxicity, and as a replacement of animal models for studying healthy and diseased tissue.

A popular manifestation of this latter aim is the creation of engineered tissue strips that have electrical and contractile activity. The force generated by these strips has been measured through various techniques and provides functional performance characteristics of the tissue. Some of these force measurement methods include a polydimethylsiloxane (PDMS) cantilever platform with optical tracking of post deflections, as well as the standard muscle bath force testing setups using several transducer technologies (Turnbull, et al., 2013). In the former, a small PDMS cast is made with two flexible posts separated at distance of ~1 cm, between which a fibrin/collagen/Matrigel-based 3D engineered tissue strip is grown. After some time in culture, the tissue will generate contractile force that causes the posts to bend. A video platform to optically track the displacement of the ends of the post due to bending enables the tissue-generated contractile force to be estimated non-invasively and in real-time using the bending equation for a cantilever beam.

These systems have a number of differences from muscle bath systems which have been used for decades to measure isolated cardiac and skeletal muscle tissue strips. One is that the PDMS-measured twitch force is non-isometric, which is contrary to muscle-bath systems. This can cause the contractile performance of the tissue to be underestimated due to the fact that the maximum force generated decreases with shortening and mechanical unloading of the tissue. Additionally, the tissue cannot be adequately stretched to its optimal length, unlike standard muscle-bath setups, which also limits the maximum force generation and complicates comparison of twitch force from different tissues. These differences can be considered drawbacks for the PDMS when trying to compare data to the abundance of previous experiments on natural tissue using muscle bath systems.

Likewise, the muscle bath also has limitations, including high expense, low throughput, non-sterile environment, and tissue damage due to clamping. Thus, there are limitations to both systems and is therefore a desire to provide a bioreactor system that can overcome the above limitations and deficiencies associated with the traditional designs.

SUMMARY

An improved tissue engineering bioreactor and testing platform has been designed that integrates multiple testing and stimulation capabilities. The system allows for growth of multiple tissue strips in parallel with mechanical and electrical stimulation, media perfusion, and the automated monitoring of contractile force and extracellular electrical activity. The system is designed to be low-cost and scalable, to provide for high-content, biofidelic, non-destructive testing of engineered muscle tissue performance that is conventionally measured using muscle-bath systems.

BRIEF DESCRIPTION OF THE DRAWING FIGURES

DETAILED DESCRIPTION OF CERTAIN EMBODIMENTS

In accordance with the present invention, an improved bioreactor system is provided that integrates features and enhances the functionality of the system, while maintaining the tissue(s) (e.g., tissue strips) constantly in an optimal incubator environment. This entails integrating all measurement and control functionality into the tissue culture system to allow automatic, real-time measurement without the need to interact with the tissues, providing improved data collection, convenience, and control of the tissues and experiments.

As discussed herein, the construction of the bioreactor system according to the present invention allows one or more tissue specimens (e.g., cardiac tissue strips) to be grown and monitored. The bioreactor system is also designed to achieve the following objectives (which is a non-limiting list) as described in detail below:

1. Ability to grow multiple tissues in culture media with controlled electrical and mechanical stimulation;
2. Ability to automatically measure the passive and active contractile forces of the tissues within the incubator, while being able to simultaneously adjust the length and tension of the tissue as well as the pacing frequency;
3. Ability to measure the action potentials generated by the tissue during the contractions; and
4. Ability to perfuse media and testing agents easily within the culture well (bath) using built-in fluid exchange ports.

Figure 1:
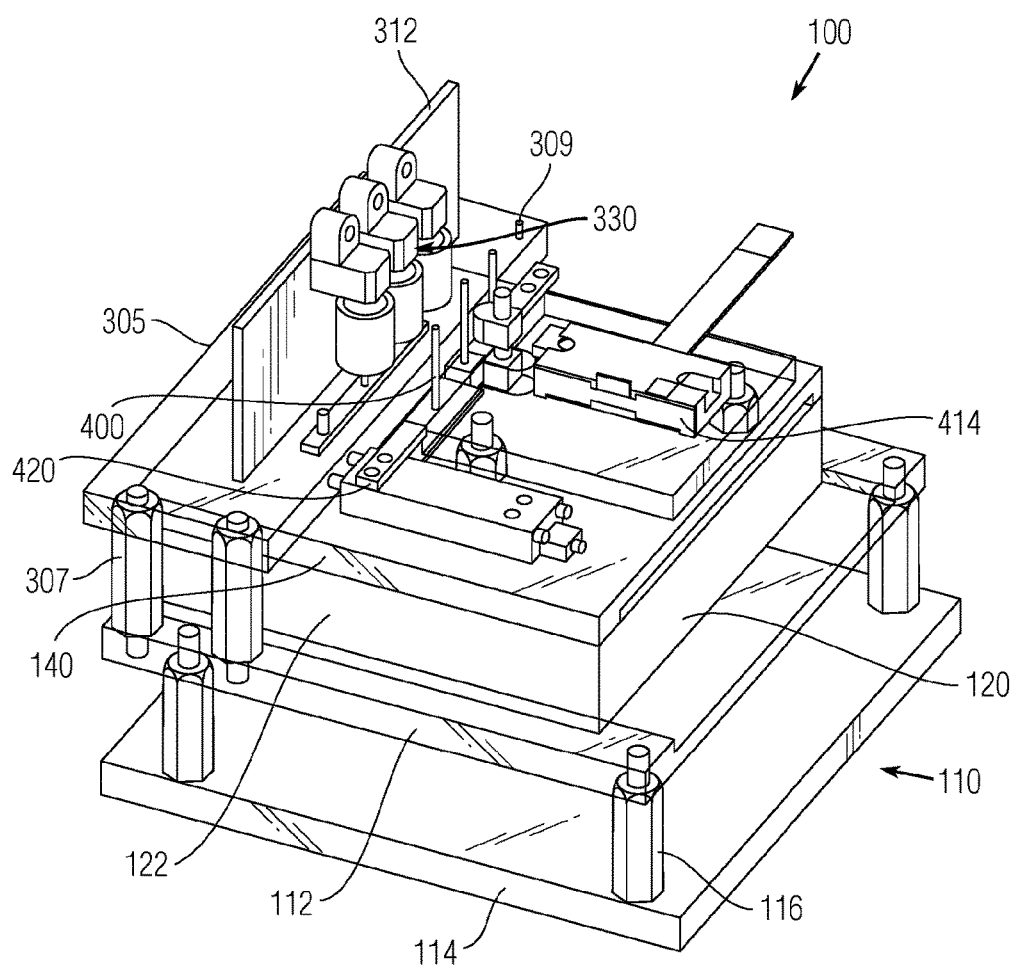
FIG. 1 is a top and side perspective view of a bioreactor system according to one embodiment of the present invention.
Figure 2:
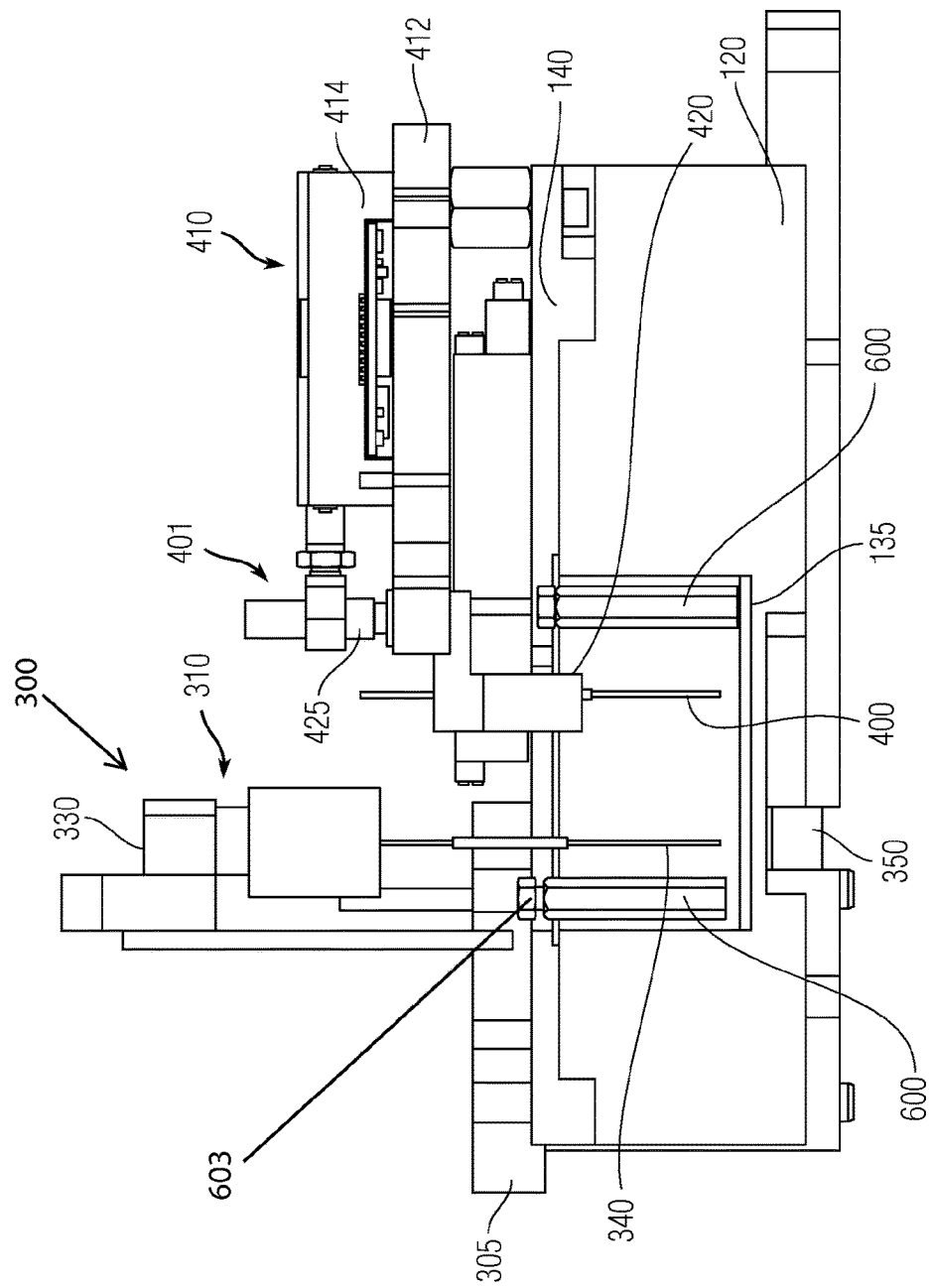
FIG. 2 is a cross-sectional view thereof.
Figure 3:
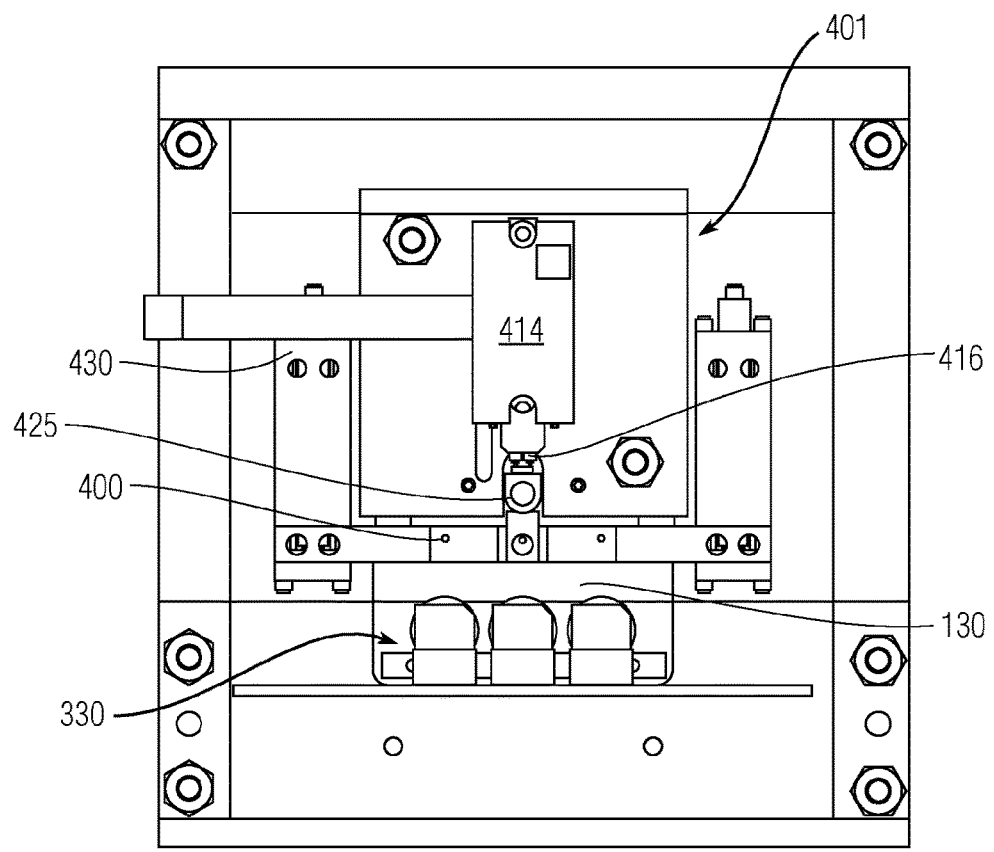
FIG. 3 is a top plan view thereof.
Figure 4:
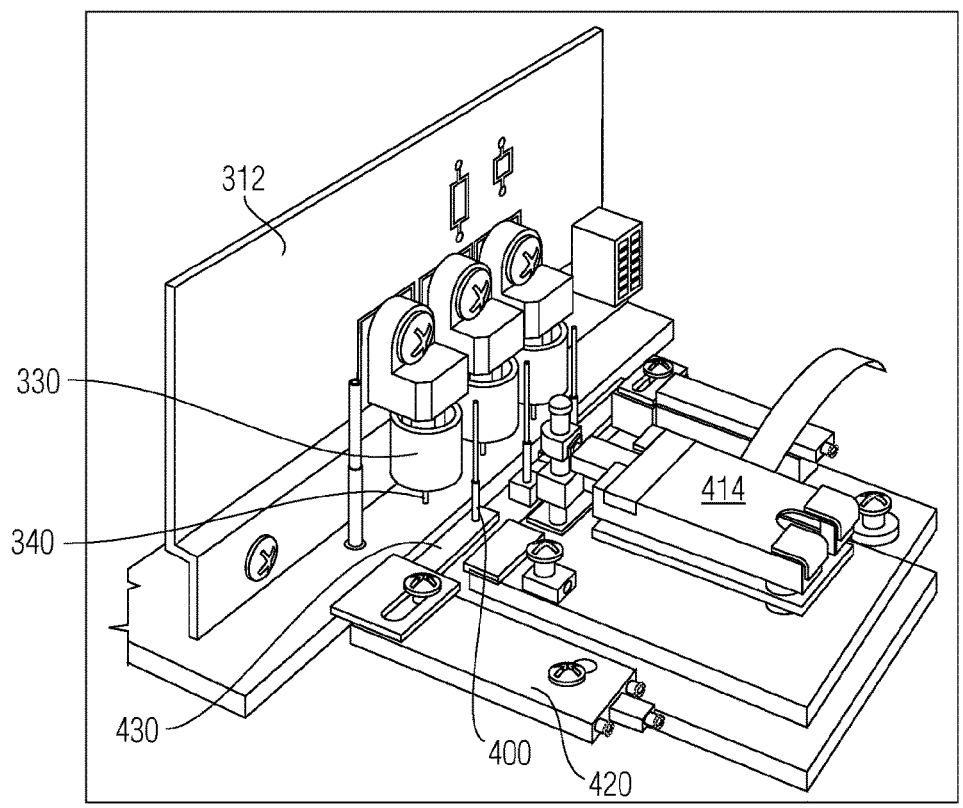
FIG. 4 is a perspective view of the bioreactor system.

FIGS. 1-4 illustrate a bioreactor system 100 in accordance with one exemplary embodiment of the present invention. FIG. 1 is a top and side perspective view of the bioreactor system 100; FIG. 2 is a cross-sectional view of the bioreactor system 100; FIG. 3 is a top plan view of the bioreactor system 100; and FIG. 4 is a perspective view of the bioreactor system 100.

The bioreactor system 100 can be, as shown, in the form of a self-contained assembly (unit) that can be placed on a support surface, such as a table or bench, or incubator shelf, or the like. As described herein, the system 100 is a powered assembly and thus is operatively coupled to a power supply, such as an electric outlet, battery, a combination thereof, etc. The bioreactor system 100 includes a bottom support 110 which supports the various working components and the electronics of the bioreactor system 100. The bottom support 110 can be in the form of a substrate or the like. In the illustrated embodiment, the bottom support 110 includes a first support 112 which is elevated relative to a second support 114 by means of a plurality of legs 116 (which can be arranged in the corners). The supports 112, 114 can be in the form of planar plate-like substrates that are arranged parallel to one another. The space between the two supports 112, 114 permits cables, visualization equipment, and the like to be routed therebetween.

It will be understood that the bottom support 110 can be in the form of a single structure and/or can take any number of different forms that are suitable for mounting the components of the system 100. Alternatively, the bioreactor system 100 does not have to be mounted to a bottom support 110 but instead can be a free standing unit that is transportable and can be disposed on a support surface, such as a table or platform.

The bioreactor system 100 further includes a base 120 which has an interior space. The base 120 is thus an at least partially hollow structure that contains other components as discussed herein. The base 120 can be formed to have any number of different shapes, including but not limited to a square or rectangular shape. The base 120 is thus defined by a floor and a plurality of side walls 122 that define the hollow interior. In the case of a square-shaped base 120, the base 120 includes four side walls 122. The base 120 can thus have an open top through which the hollow interior can be accessed.

As shown, the base 120 can be disposed on the first support 112 of the bottom support 110. The base 120 can be securely mounted to the first support 112 or can simply rest on the first support 112.

The bioreactor system 100 further includes a culture well (bath) 130 that is disposed within the hollow interior of the base 120. The position and construction of the culture well 130 are described in detail below. In general, the culture well 130 represents a well in which the engineered cardiac tissue is grown and also tested in the case of the present bioreactor system 100. The culture well 130 can thus be disposed along the floor of the base 120.

As best shown in FIG. 2, a bottom (floor) of the culture well 130 can be defined by a transparent structure (light transmissive) 135, such as a glass slide. The dimensions, such as height, of the culture well 130 are defined by the height of the base 120.

The bioreactor system 100 can also include a lid 140 which mates with the base 120. The lid 140 thus closes off the open top of the base 120. The lid 140 can thus be a planar structure that seats across the open top of the base 120 for closing off the hollow interior of the base 120. The lid 140 can have a planar top surface 142 to which equipment is mounted. The lid 140 is removable from the base 120. As described herein, during assembly of the system 100, the lid 140 is lowered onto the base 120 so as to close off the base 120. Any number of different locating, coupling and/or locking mechanisms can be used to securely attach the lid 140 to the base 120.

The bioreactor system 100 also includes a force sensor assembly (force sensor/force sensing device) 300. The force sensor assembly 300 is configured to measure the passive and active contractile forces of the tissue being grown in the culture well 130, while being able to simultaneously adjust the length and tension of the tissue.

The force sensor assembly 300 according to one embodiment of the present invention includes two main components, namely a first sensor component 310 and a second sensor component 350. The first sensor component 310 is constructed such that a portion thereof extends into the culture well 130, while the second sensor component 350 is disposed outside of the culture well 130.

The force sensor assembly 300 can be mounted to a support 305 that is separate from the lid 140 and the base 120. The support 305 is designed to fixedly position and hold the force sensor assembly 300 in a fixed location relative to the culture well 130 (and thus relative to the lid 140 and the base 120). The support 305 can be in the form of a planar substrate (as shown) that is positioned above the lid 140 when the lid 140 is coupled to the base 120. For example, the support 305 can be mounted to the support 112 in an elevated manner and in particular, the support 305 can be elevated relative to the support 112 by means of a plurality of legs 307. The legs 307 contact and rest against the support 112 and more specifically, the legs 307 are fixedly attached to the support 112 so as to lock the assembly 300 in place over the lid 140. The assembly 300 can thus be both detachable and removable from the support 110 and at the same time fixedly locked in a set position relative to the support 110 and thus relative to the base 120 and lid 140.

The support 305 can be thought of as a base for the assembly 300 and allows the equipment of the force sensor assembly 300 to be mounted thereto. The support 305 extends transversely across a width of the base 120 and the lid 140. The support (base) 305 has a top surface 309. The support 305 can include electronics that are associated with the assembly 300. For example, a printed circuit board 312 can be provided that is mounted to the support 305, and provides mounting for first sensing component 310, as well as connectors for power and other signals to external control, amplification, and/or data acquisition devices. While the circuit board 312 is shown as being vertically mounted relative to the support 305, the circuit board 312 is not limited to being in such orientation but instead can be disposed in other orientations, such as being mounted horizontally.

The first sensor component 310 is in the form of a light emitting member and more specifically comprises at least one light source which is configured to direct light along a defined axis in a desired direction. In one variation, the first sensor component 310 comprises a vertically mounted LED light source such that the light emitted from the LED light source is directed downwardly, through the fiber-optic tissue post 340, along an axis that is perpendicular to lid 140.

In the illustrated embodiment, the first sensor component 310 includes a plurality of light sources and more specifically, includes a plurality of LED light sources in one variation. For example, in the illustrated embodiment, there are three LED light sources 310 that are mounted to the circuit board 312 (and operatively connected to the processor 312). The three LED light sources 310 can be mounted linearly along the same axis. The axes of the light that is emitted from the three LED light sources 310 are parallel to one another and are in a spaced relationship. Each LED light source 310 thus includes its own LED for emitting light, but could also be coupled to a common light source.

In accordance with the present invention, each LED light source 310 comprises a fiber-optic LED emitter 330 and an associated fiber-optic tissue post 340 that is operatively coupled to the fiber-optic LED emitter 330 to allow light to be projected through the fiber-optic tissue post 340. The fiber-optic tissue post 340 is thus formed of a fiber-optic. As is known, a fiber-optic is a flexible, transparent fiber made of extruded glass (silica) or coated plastic and the fiber-optic acts as a waveguide or light pipe to transmit between the two ends of the fiber-optic. The fiber-optic LED emitter 330 thus serves to emit light from an LED light source (bulb) to the fiber-optic which in this case is in the form of a fiber-optic tissue post 340. This alignment between the emitter 330 and the fiber-optic tissue post 340 results in light being directed downward in the culture well 130 and more specifically, the light is directed axially toward the second sensor component 350 which detects the light as discussed herein.

The first sensor component 310 extends below both the support 305 and the lid 140 and therefore, these two structures are configured to accommodate each of the fiber-optic tissue posts 340. For example, the lid 140 can have openings through which the fiber-optic tissue posts 340 pass through. The fiber-optic tissue posts 340 are axially aligned and positioned within the culture well 140 such that they are generally perpendicular to the floor of the culture well 140 and are parallel to one another and are axially aligned. The openings formed in the lid 140 can have seal members, such as rubber gaskets, O-rings, etc.

The bioreactor system 100 can be assembled in any number of different ways and the order or assembly can vary depending upon the construction of the parts. For example, the support 305 can be mounted after the lid 140 is mounted to the base 120 since the support 305 extends over and across the lid 140. The circuit board 312 associated with the fiber-optic tissue posts 340 allows for providing power the fiber-optic LED emitters 330, as well as other connections to pacing electrodes 600, metal tissue posts 400, and other locally or externally contained circuit boards.

The second sensor component 350 can be in the form of a sensor (e.g., a position sensitive detector (PSD)) that is disposed below the transparent floor 135 (glass slide) of the culture well 130 and is configured to detect movement of the first sensor component 310 (posts 340). The operation of the second sensor component 350 is described in detail below.

The bioreactor system 100 also includes one or more movable tissue posts 400 that are also disposed within the culture well 130 and are part of a tissue post assembly 401. In accordance with the present invention, there are a plurality of movable tissue posts 400 (e.g., three in the illustrated embodiment) and the number of movable tissue posts 400 is equal to the number of fiber-optic tissue posts 340. The movable tissue posts 400 are arranged such that they face and are spaced from the fiber-optic tissue posts 340 and therefore, one set of posts is comprised of one fiber-optic tissue post 340 and one movable tissue post 400. In the illustrated embodiment, there are thus three sets of posts since there are three fiber-optic tissue posts 340 and three movable tissue posts 400. Each set of posts 340, 400 serves as a means for growing tissue therebetween as discussed below.

The movable tissue posts 400 are operatively coupled to a mechanism 410 which controllably moves the tissue posts 400 and more particularly, moves the tissue posts 400 in a controlled linear manner. These posts are intended to be rigid and electrically conductive, so as to not bend and to act as a sensing electrode of the tissues' electrical activity. The mechanism 410 can be in the form of an actuator, such as a linear actuator, that controllably moves the tissue posts 400 in a linear direction. The linear actuator includes a motor, such a stepper motor, which allows for precise control over the movable tissue posts 400.

The tissue post assembly 401 is configured to be fixedly attached to the top surface of the lid 140. When the mechanism 410 is in the form of a linear actuator, the mechanism 410 can include an actuator base 412 which is coupled to the lid 140 and an actuator module 414 (e.g., a linear motion module). The mechanism 410 includes a drive shaft 416 that is controllably driven by a motor contained within the actuator module 414. The drive shaft 416 can extend outwardly from the front of the actuator module 414 in a direction towards the posts 340, 400.

The tissue post assembly 401 also includes a post holder 420 which is coupled to linear slides 430 and carries the tissue posts 400 such that movement of the post holder 420 is directly translated into movement of the tissue posts 400. The linear slides 430 are frictionless slides that permit the post holder 420 to be moved in a controlled manner in a linear direction. A linkage 425 couples the drive shaft 416 to the post holder 420 and translates the motion of the drive shaft 416 to the post holder 420 which carries the tissue posts 400. The post holder 420 can thus at least include a transverse member that extends across the width of the base 120 and lid 140 and the slides represent spaced apart parallel arms that extend rearwardly from the transverse member of the post holder 420.

The tissue post assembly 401 is also operatively connected to a main controller (e.g., processor) that allows for the controlled and precise movement of the tissue posts 400 based on user inputted instructions (input). The main controller is thus in communication with the actuator module 414 (motor) and controls the driving of the drive shaft 416 and thus, movement of the post holder 420 and the tissue posts 400 in a linear direction. Under operation of the actuator module 414, the tissue posts 400 can be driven in a direction toward the fiber-optic tissue posts 340 (thereby reducing the spacing between the posts 340, 400) or in a direction away from the fiber-optic tissue posts 340 (thereby increasing the spacing between the posts 340, 400) or any combination of these movements to generate arbitrary linear stretch/shortening regimens. In the illustrated embodiment, the movable tissue posts 400 are in the form of tungsten posts to provide a thin, stiff, biocompatible tissue mount that are also capable of detecting extracellular electrical conductivity when connected to inputs of appropriate amplifier.

When the lid 140 is assembled to the base 120, the movable tissue posts 400 and the fiber-optic tissue ports 340 are disposed within the culture well 130 with the distal (bottom) ends thereof being spaced from the floor of the culture well 130.

As explained below, the fiber-optic tissue posts 340 are flexible in nature and are suspended within the culture well 130 and therefore, when a sufficient force is applied, the fiber-optic tissue posts 340 exhibit flexing (a degree of lateral displacement of free end) while the stiff (tungsten) tissue posts 400 remain straight without flexing.

Figure 6:
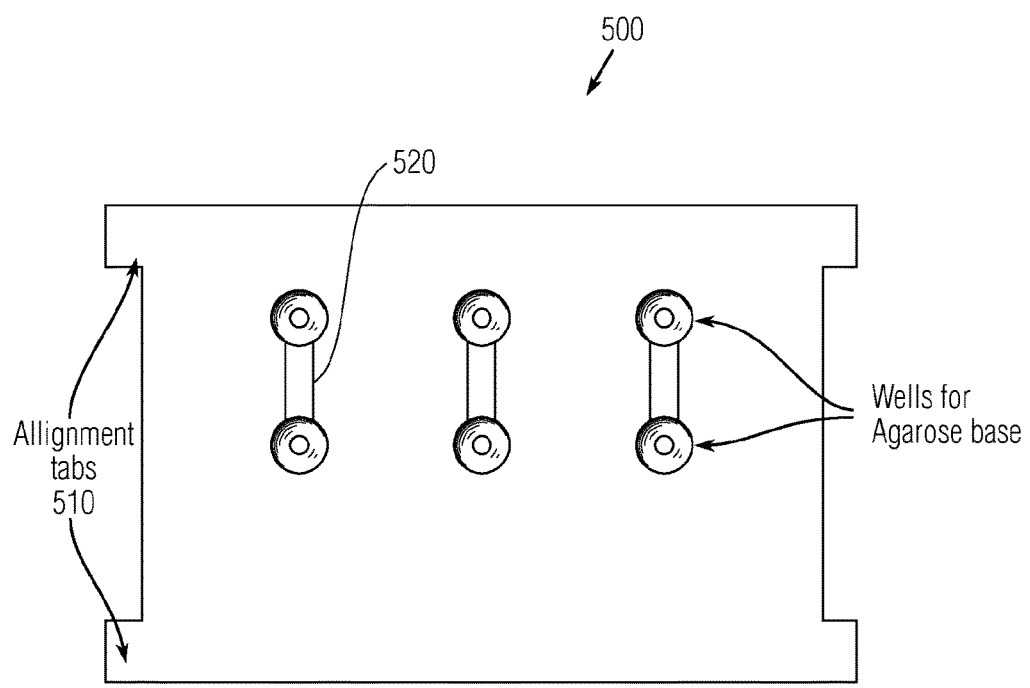
FIG. 6 is a top plan view of a multi-tissue casting mold.

As shown in FIG. 6, a tissue-casting mold 500 can been fabricated from a suitable non-adherent material, such as Teflon®, that is placed at the bottom of the culture well 130, aligned by tabs 510 that fit into slots on either side of the well 130 (See FIG. 6). Three dog-bone shaped wells 520 sit under the posts 340, 400 (FIGS. 2 and 3) so that the tissue forms around the posts 340, 400. The ends of the mold are deeper than the length portion of the mold, providing a well that is filled with melted agarose. Once the agarose cools into a firm hydrogel, the posts 340, 400 are pushed through the agarose into the wells, and the tissue forms on top of the agarose so that the ends of the posts 340, 400 are exposed once the tissue is removed from the mold.

Tissues (e.g., tissue strips) are formed according to a protocol developed by the Costa Lab using the previous PDMS system (Serrao, et al., 2012). Briefly, about 30 µl of the ice-cold collagen-matrigel-cell mixture is pipetted into each well, the lid is then placed on such that the tungsten and fiber-optic posts 400, 340 align with the deeper end pockets of the casting mold 500 and pierce the agarose, which is then incubated for 2 hours before culture media is added. The lid 140 is carefully lifted up after 48 hours to remove the tissues from the casting mold 500, the mold 500 is removed, electrodes are easily re-connected using a magnetic pin interface, and the lid 140 is re-installed. The system is then ready for normal operation and measurements.

A perfusion system can be implemented using ports in the sides of the culture well 130 and out the sides of the bioreactor system 100. This allows for a press-fit stopcock or similar coupling device to be connected along with tubing to circulate or exchange culture media.

The bioreactor system 100 is a computer implemented system and can include one or more computing devices and in one aspect, the bioreactor has a means of communicating with an external computing system through a data acquisition and control interface. The computing device can be in the form of a personal computer, a mobile device, a tablet, a work pad, etc. The computing device includes one or more processors used to execute software code in order to control the operation of data processing apparatus, read only memory (ROM), random access memory (RAM) or any other suitable volatile or non-volatile computer readable storage medium, which can be fixed or removable. The system 100 also preferably includes one or more network interfaces to transmit and receive data to and from other computing devices across a communication network. The network interface can be any interface that enables communication between any of the devices and includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting the devices and/or communication networks, such as private networks and the Internet. Such connections can include a wired connection or a wireless connection (e.g., using the IEEE 802.11 standard known in the relevant art) though it should be understood that network interface can be practically any interface that enables communication to/from the processor.

The computing device used in system 100 includes memory and typically, includes a storage device. Storage device(s) can be included such as a hard disk drive, floppy disk drive, tape drive, CD-ROM or DVD drive, flash memory, rewritable optical disk, rewritable magnetic tape, cloud storage, or some combination of the above for storing program code, databases and application code. In certain implementations, memory and/or storage device(s) are accessible by the processor, thereby enabling the processor to receive and execute instructions stored on the memory and/or on the storage. Further, elements include one or more input devices such as a keyboard, mouse, track ball and the like, and a display. The display can include a screen or any other such presentation device that enables the system to instruct or otherwise provide feedback to the user regarding the operation of the system (100). By way of example, display can be a digital display such as an LCD display, a CRT, an LED display, or other such 2-dimensional display as would be understood by those skilled in the art. By way of further example, a user interface and the display can be integrated into a touch screen display. Accordingly, the display is also used to show a graphical user interface, which can display various data and provide "forms" that include fields that allow for the entry of information by the user. Touching the touch screen at locations corresponding to the display of a graphical user interface allows the user to interact with the device to enter data, control functions, etc. So when the touch screen is touched, interface communicates this change to processor, and settings can be changed or user entered information can be captured and stored in the memory.

One or more software modules can be encoded in the storage device(s) and/or in the memory. The software modules can comprise one or more software programs or applications having computer program code or a set of instructions executed in the processor. Such computer program code or instructions for carrying out operations or aspects of the systems and methods disclosed herein can be written in any combination of one or more programming languages, as would be understood by those skilled in the art. The program code can execute entirely on one computing device (e.g., data processing apparatus) as a stand-alone software package, partly on one device and partly on one or more remote computing devices, such as, a user computing device, or entirely on such remote computing devices. In the latter scenario, the various computing devices can be connected to the media server data processing apparatus through any type of wired or wireless network, including a local area network (LAN) or a wide area network (WAN), or the connection can be made to an external computer (for example, through the Internet using an Internet Service Provider). It should be understood that in some illustrative embodiments, one or more of the software modules can be downloaded over a network from another device or system via the network interface. For instance, program code stored in a computer readable storage device in a server can be downloaded over a network from the server to the storage.

Fiber-Optic Force Sensor

As mentioned herein, the first and second sensor components 340, 350 serve as a fiber-optic force sensor. The optical fiber (first sensor component) 340 is suspended vertically in the culture well 130, with the tissue grown at the ends of the fiber 340. The fiber-optic tissue post 340 serves as both a light guide to the second sensor component 350 which is in the form of a position-sensitive detector (PSD) 350, as well as a cantilever for measuring tissue contractions. The position-sensitive detector 350 is an optical position sensor that can measure a position of a light spot in one or two-dimensions on a sensor surface (the PSD utilizes photodiode surface resistance to determine the position (location) of the light spot). In the present case, the light spot is generated by the fiber-optic LED emitter and passes through the fiber-optic before creating the light spot on the position-sensitive detector 350. The PSD 350 is disposed below the glass slide that forms the floor of the culture well 130 and allows for passage (transmission) of the light that is emitted from the open distal end of the fiber-optic tissue post 340. The PSD 350 are connected to trans-impedance amplifiers configured to amplify convert the low currents generated by the PSD 350 into a measureable voltage.

The following information details the mechanical properties of one exemplary fiber-optic tissue post 340 and how it relates to the force measurement capacity (it will be understood that the following dimensions and characteristics are only exemplary and not limiting of the present invention):

Diameter of fiber: 0.5 mm (CK-20, Industrial Fiber-optics, Inc.)

Modulus of fiber E: 4 GPa

Figure 5:
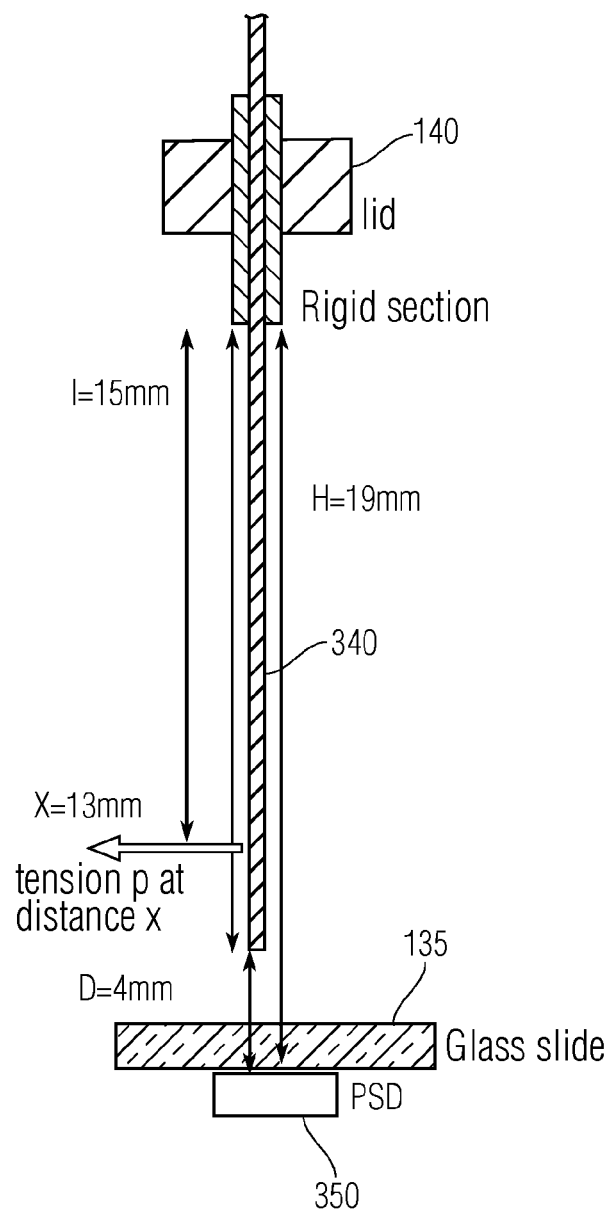
FIG. 5 is a cross-sectional view of a fiber-optic post that acts as a fiber-optic tension sensor.

The fiber properties and its configuration determine its response to tension and the resulting detected photodiode signal (see FIG. 5). FIG. 5 is a cross-sectional view that shows the fiber-optic tissue post 340 depending downward from the lid 140 with the upper portion of the fiber-optic (post 340) being a more rigid portion. As shown, the free, distal end of the fiber-optic tissue post 340 is spaced from the glass slide that is disposed above the second sensor component 350.

The tension p is assumed to occur at one point on the fiber, at distance x from the fixed end. The lateral displacement γ at x is then:

$$\gamma = \frac{px^2}{3EI} \qquad \text{Equation 1}$$

where I is the area moment of inertia for a cylindrical beam of radius r:

$$I = \frac{\pi r^4}{4} \qquad \text{Equation 2}$$

As shown in FIG. 5, the deflection γ at point x represents the length change of the tissue that is attached between the fiber-optic tissue post 340 and the movable tissue post 400. This does not indicate the displacement of the light spot on the sensor (PSD) 350, which is also dependent on the length of the fiber 340, the bending angle of the fiber 340, and the distance of the end of the fiber 340 from the sensor 350.

The deflection of the end of the end of the fiber d is given by:

$$d = \frac{px^2(3l-x)}{6EI} \qquad \text{Equation 3}$$

The angle $\theta_x$ of the beam end to point x relative to the vertical is given by:

$$\theta_x = \frac{px^2}{2EI} \qquad \text{Equation 4}$$

This angle produces additional lateral displacement δ of the light beam as it travels distance D to the sensor (PSD 350) given by:

$$\delta = D \tan \theta_x \qquad \text{Equation 5}$$

Total spot displacement Δ is given by:

$$\Delta = d + \delta \qquad \text{Equation 6}$$

The following parameters and values were used to model the system:

TABLE 1

Parameters for modeling beam behavior of tension sensor

| Parameter | Description | Value | Units |
|---|---|---|---|
| r | Radius of optical fiber | 0.25 | mm |
| l | Length of optical fiber from base to tip | 15 | mm |
| x | Distance from base to tissue force | 13 | mm |
| D | Distance from fiber tip to optical sensor | 4 | mm |
| E | Young's modulus of optical fiber | 4.2 | GPa |
| p | Point force applied by tissue on fiber | 0-1000 | μN |

Figure 7:
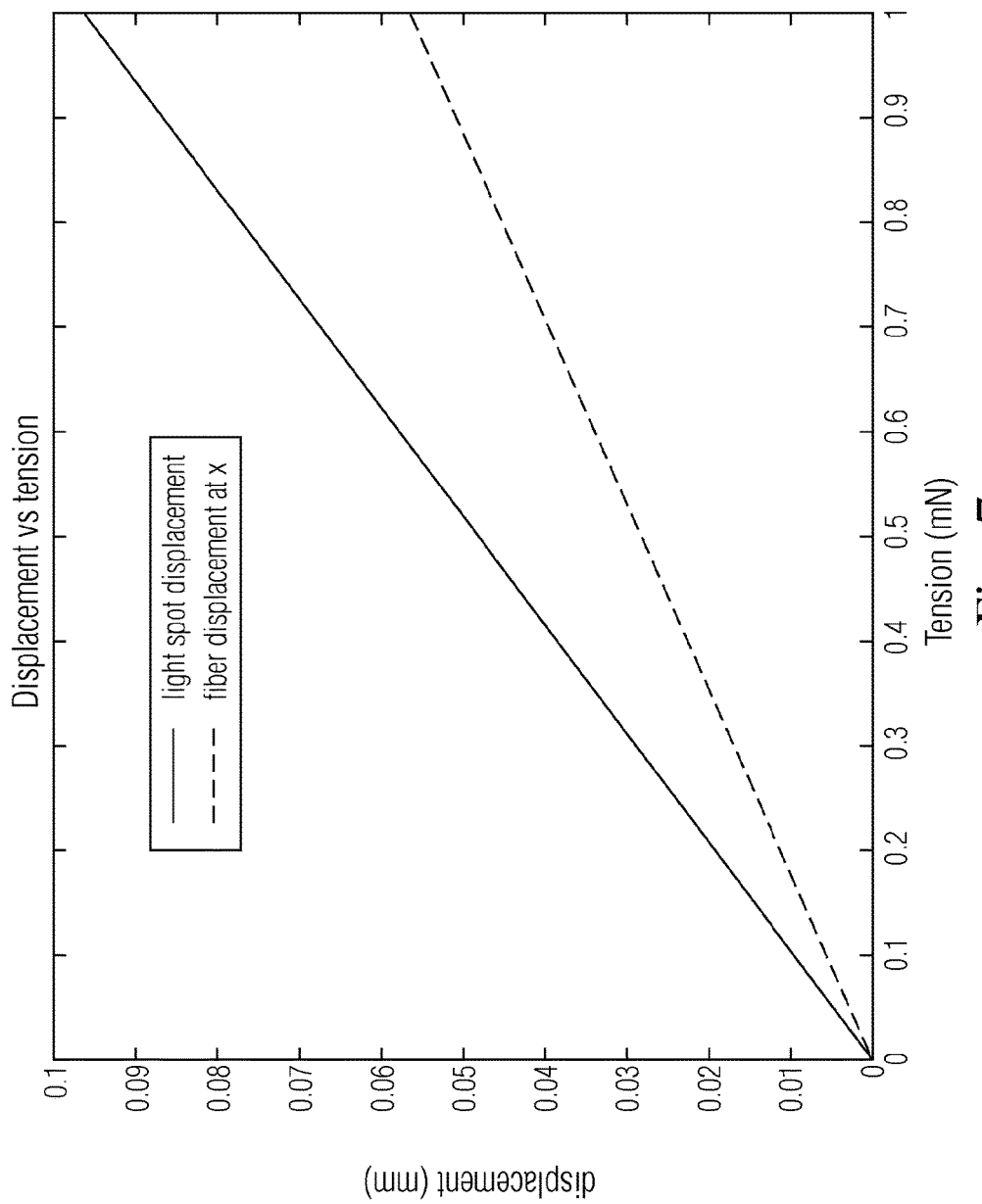
FIG. 7 is a graph of displacement vs. tension for the parameters set forth in Table 1, demonstrating a nearly 2-fold amplification of the tip deflection signal (based on the light spot compared to the actual fiber optic tip displacement at the site of applied tissue force) to increase sensitivity to the applied force.

FIG. 7 is a graph of displacement vs tension for parameters given in Table 1. The two curves show the fiber displacement at x due to tissue contraction (i.e., γ in equation 1) and the resulting light spot displacement (i.e., Δ in the above equation). Note how the force sensor design provides increased deflection sensitivity to tissue contraction force (signal gain).

Fiber-Optic Force Sensor—PSD Amplifier Design

Figure 8:
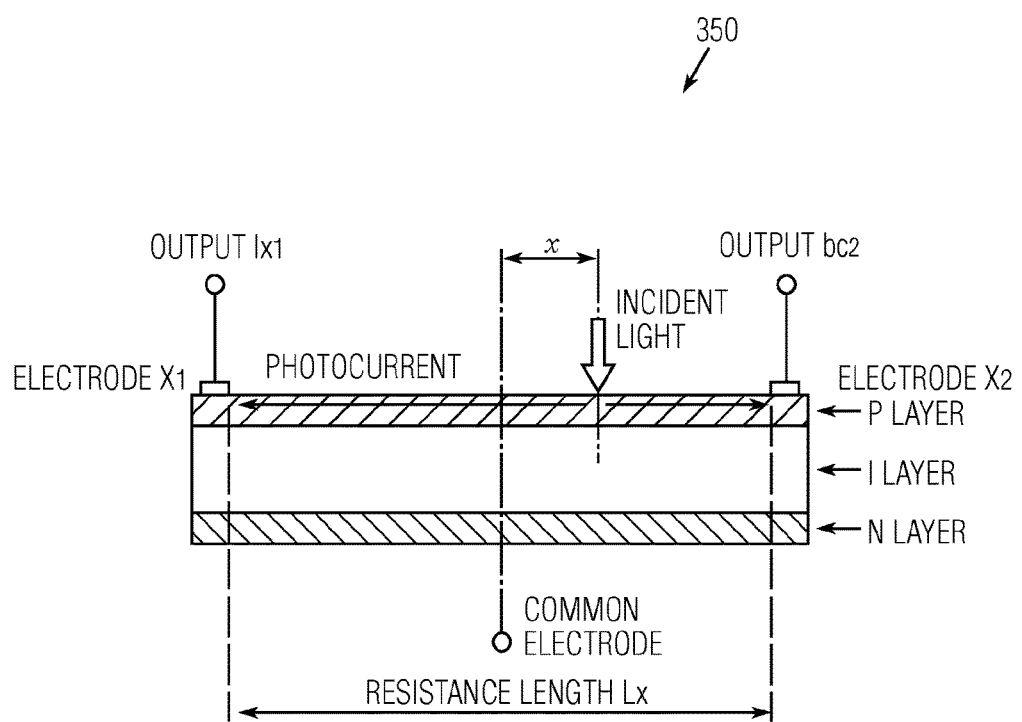
FIG. 8 is a cross-sectional view of a position sensitive detector (PSD) for use with the fiber-optic post of FIG. 5.

The position-sensitive detector (PSD) 350 includes an amplifier that has a sensing region length of 3 mm. The sensor 350 is a lateral photodiode with two electrodes on either end of the anode, and a common cathode. The light beam from the optical fiber is received by the anode region of the PSD 350, which acts as a current divider between two electrodes, distributing current based on the light spot proximity to either electrode. FIG. 8 is a cross-sectional view illustrating the structure of the PSD 350.

One exemplary sensor 350 used is a Hamamatsu S8673 PSD. The LED light source (fiber-optic 340) can be a fiber-optic that is commercially available under the trade name Industrial Fiber-Optics IF-E92B.

The LED can have a wavelength of 470 nm, and the incident light power on the sensor 350 is estimated to be 20 μW. The PSD 350 can have a sensitivity of 0.2 A/W at 470 nm, which will result in a total current $I_o$ of 4 μA.

The current through each electrode of the PSD 350 is given by:

$$I_{x1} = \frac{\frac{L_x}{2} - x}{L_x} = I_o \qquad \text{Equation 7}$$

For $L_x$ of 3 mm, a change in x of 0.05 mm, and an $I_o$ of 4 uA, the change in current through each electrode is ~67 nA. For the desired smallest detectable change at 0.005 mm, the current is 6.7 nA. A full-scale estimate of the detection range is 0.1 mm, producing a difference of 0 to 150 nA between electrodes.

A dual-transimpedance amplifier, such as one that is commercially available under the trade name ADA4000-2, can be used to amplify the current from each electrode. The amplifier has a Gain-Bandwidth Product (GBP) of 5 MHz, and an input capacitance of 5 pF. The initial board will have a 1 Mohm feedback resistor in parallel with a 10 pF feedback capacitor. The maximum range of output from the PSD amplifier in its current configuration has been tested to be from 0 to −7.7 V. This is due to the fact that only negative current can occur through each electrode. Another suitable board can use a voltage divider offset applied to the non-inverting input of the op-amp to provide an effective range of +7 to −7 V. This will allow the use of a larger feedback resistor and increased full-scale output. In the current design the output $E_o$ for a 2 µA input through each electrode is:

$$E_o = -\text{Isignal} * R_f + V_{os} = -2e-6*1e6+0V = -2V \qquad \text{Equation 8}$$

For a current swing of 150 nA, this corresponds to a 0.15 V output swing from each electrode (and a net difference of 0.3 V). This can be increased by modifying the circuit as described previously.

The raw voltage signal from each amplified electrode current is acquired by a data acquisition instrument, such as National Instruments DAQ, and processed using appropriate software, such as LabVIEW. The voltage from each electrode for one sensor is put through the following formula to obtain what is called the "normalized difference voltage" (NDV):

$$NDV = \frac{(VA - VB)*10}{VA + VB} \qquad \text{Equation 9}$$

The normalized difference voltage for the full-scale swing of 0.15 volt can then be calculated as follows:

NDV=(2.15−1.85)*10/(2.15+2.85)NDV=0.75NDV

This means the system will produce a signal from 0 to 0.75 NDV for a force range of roughly 0 to 1000 µN.

The NDV signal is calibrated to the displacement of the fiber to measure force. The (semi-automated) calibration procedure described below is performed prior to the start of each use of the system to grow and test tissues.

It will be appreciated that the above equipment and above described dimensions and values and procedures are merely exemplary in nature and not limiting of the scope of the present invention.

In accordance with the present invention, the bioreactor system 100 is disposed within an incubator or the like which is operated under conditions ("incubating conditions") that promote tissue growth within the culture well 130 between the posts 340, 400.

Enclosures for a power supply, the extracellular action potential amplifier, and PSD amplifier are housed in the incubator along with the bioreactor, with Ethernet cables (or other communication cables) running from the amplifiers to the DAQ to carry the signals to and from a remote desktop computer. Alternatively, wireless communication can be implemented between the various computer equipment and bioreactor components of the present invention. The M3-L implementation of actuation module 414 uses a USB cable. Flat patch cable is used to run through the front door jamb or rear instrumentation port of the incubator.

In constructing the bioreactor system 100 and performing the calibration procedure described above, all three optic fibers are cut to length and carefully placed into their LED shafts, and the motor post holder which normally holds tungsten wires for tissues, is replaced with a crossbar extension that runs behind the fibers. This crossbar pulls laterally on the fibers simultaneously at a carefully selected height (to match the height of the tissues), and a LabVIEW routine records the PSD output versus the position. A linear plot of NDV versus position is produced, of which the slope of the line-fit is the sensitivity in NDV/µm.

A Matlab script is used to calculate the force sensitivity based on this calibration value and on the fiber geometry and displacement height. Given a displacement sensitivity k in units of µm/NDV, the formula for force sensitivity FS in units of µN/NDV is as follows:

$$FS = \frac{3kEI}{x^3} \qquad \text{Equation 10}$$

Figure 9:
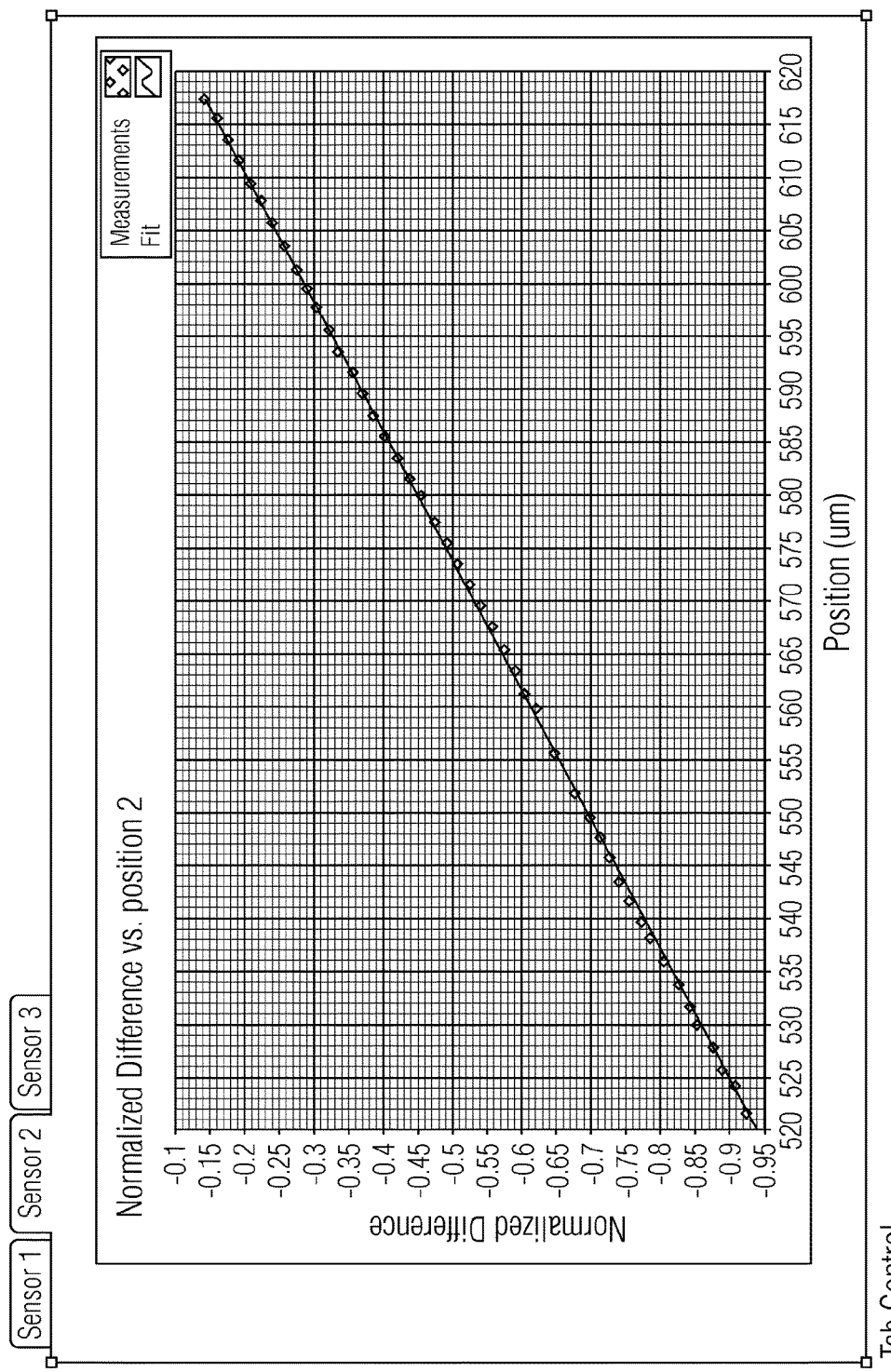
FIG. 9 is a graph of normalized difference voltage (NDV) vs. deflection output from a calibration program, showing excellent linearity.

In order to minimize estimation errors, the calibration bar must apply the displacement at the exact height at which the tissue will be grown, and this height should be measured for each fiber with an image-based approach to verify the measurement and account for adjustments during post-processing analysis of the twitch force. If the height differs from where the tissue resides, a more complex model will be needed to convert to force from NDV, based on the equations listed in the previous section (See, e.g., the third to sixth equations listed above). A representative calibration graph is shown below in FIG. 9. The graph shows the high linearity of the sensor output over a large 100-micron deflection range.

Length and Loading Control

The bioreactor system 100 of the present invention is designed to provide length control of the tissues at a resolution of 1 micron. A piezoelectric-driven miniature linear actuator by NewScale Technologies provides absolute position control at a resolution of +/−0.5 micron, with tunable speed and acceleration. The motor is controlled via the LabVIEW control software and communicates via USB. The shaft of the actuator is coupled to the tungsten tissue posts 400 opposing the optic fiber sensing posts 310. The tungsten posts 400 are mounted in a holder held above the culture dish by miniature linear ball bearing slides, and the motor pushes and pulls on the holder, moving all three tissues identically (See FIG. 3 and FIG. 4). It should be noted that other linear actuator technologies, such as stepper-motor driven actuators can be implemented to provide the same function.

This functionality provides a great advantage over PDMS and other systems without length control, such as allowing mechanical stimulation of the tissue, determining physiologically optimal length (known to cardiac specialists as $L_{max}$), and performing experiments to measure the contractile force-length relationship. Additionally, this allows measurement of the active and passive tissues stiffness, and also permits load-controlled rather than length-controlled tissue testing protocols.

Electrical Stimulation and Monitoring

The bioreactor system 100 also incorporates electrical stimulation via carbon electrodes 600 for tissue maturation and pacing, as well as amplifiers for monitoring the extracellular electrical activity of the tissues. The stimulating electrodes 600 can be in the form of parallel graphite plates positioned at either end of the tissues strips (grown between the posts 310, 400) in order to produce an electric field across the length of the tissue. The electrodes 600 can be connected via stainless steel tube connectors with one or more embedded magnets that slide up stainless steel dowel pins on the lid 140. This facilitates easy electrode removal and re-insertion during the course of the experiment, where the electrodes 600 will need to be swapped and cleaned due to electrolysis byproduct buildup. Electrical connection to the stimulation wiring is made through the steel pins 603 associated with the lid 140.

The pulse waveform is controlled using a controller/software, such as LabVIEW which is described in more detail herein. A biphasic square wave pulse with controllable duration, amplitude, and frequency is configured and sent to the electrodes 600 from the analog output ports on the data acquisition interface (DAQ). This provides a simple, inexpensive, and effective means to stimulate and pace the tissues during culture and during experiments at various time points throughout the lifetime of the tissue.

The present invention can employ the use of a biopotential amplifier and in particular and according to one embodiment, a set of bioelectric amplifiers can be constructed based on the design by Bruce Land of Cornell University, as outlined in his 2001 publication, "Tools for Physiology Labs: An Inexpensive High-Performance Amplifier and Electrode for Extracellular Recording" (Land, et al., 2001). The amplifier is connected in a monopolar measurement configuration, with the tungsten wire acting as the measurement electrode, and a silver-silver chloride wire placed under the opposite graphite plate to provide a common reference electrode. It will be appreciated that the above amplifier is merely exemplary in nature and others can be used.

Controller/Software

As mentioned herein, the bioreactor system 100 is part of a computer implemented system and software is used to control the operation of the various components of the bioreactor system 100 as well as measure and record data during a test/experimental mode.

For example, a LabVIEW program has been developed to provide real-time control and data acquisition to the bioreactor throughout the entire duration of the experiment, which could last 3 weeks or more. The LabVIEW program simultaneously monitors the force and electrical activity of all three tissues, as well as controlling the motor and electrical stimulation. Intermittent data logging and electrical pacing can be set to occur at a user-prescribed interval and duration. Two experiment modules have been implemented to study force versus length and force versus pacing frequency. These modules allow the user to increment length or pacing frequency at prescribed increments and durations. The motor can also be set to oscillate between two points to provide cyclical stretch stimulation of the tissue.

Figure 10:
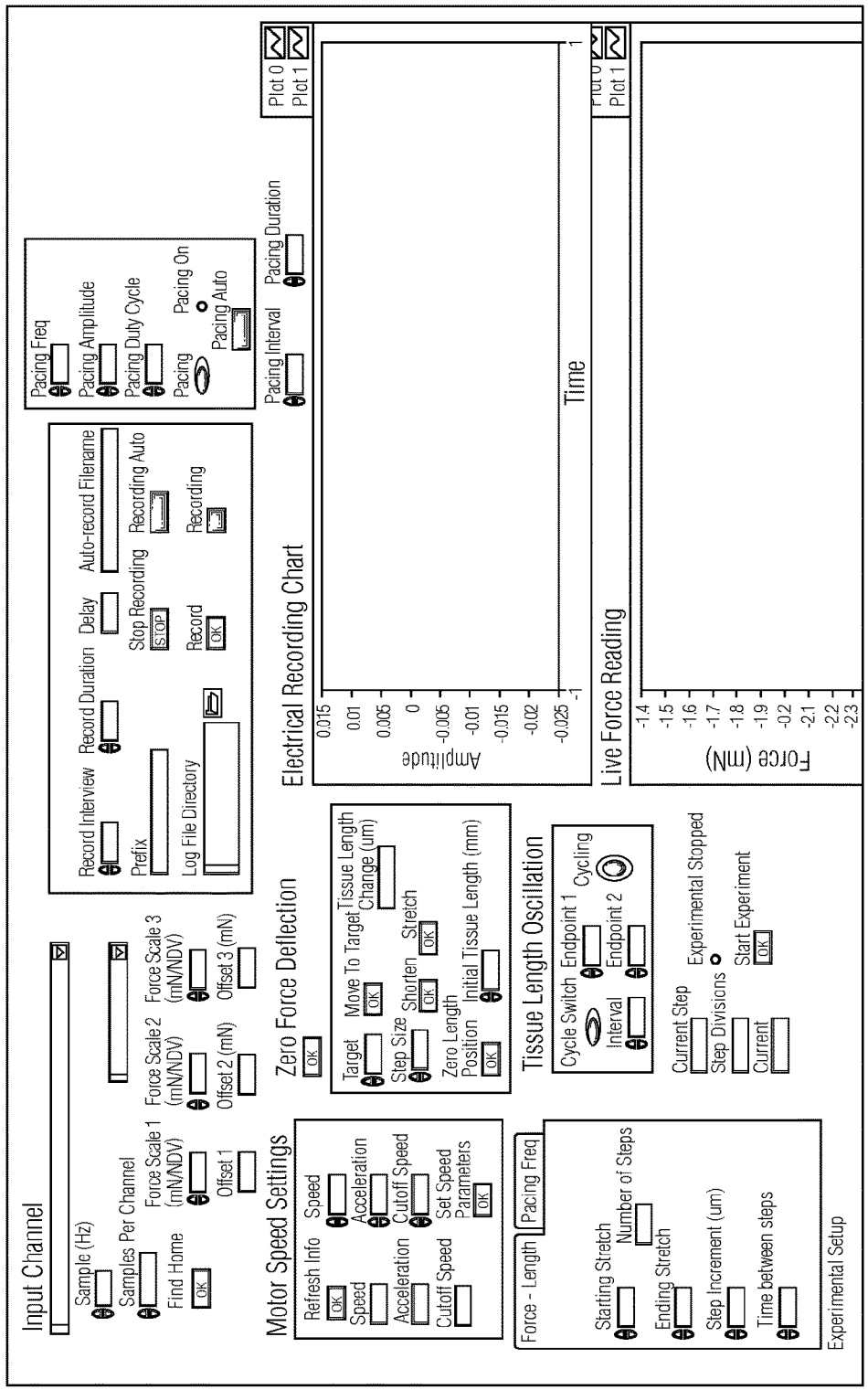
FIG. 10 is a display screen of software that is configured to control the various components of the bioreactor system and measure and record information.

FIG. 10 is a screen shot of one exemplary LabVIEW control program.

As described in detail herein and with reference to the attached figures, the bioreactor system 100 is designed to achieve the following objectives:

Objective 1—Ability to Grow Multiple Tissues in Culture Media with Controlled Electrical and Mechanical Stimulation The first objective is accomplished using a CNC manufactured sheet of polysulfone that contains the culture well 130 and supports the tissue and stimulatory components. Mechanical stimulation is implemented with the miniature linear actuator 414 with closed loop absolute position control (see details in the second objective). The arm of the actuator is connected, in one variation, to an array of three 0.5 mm diameter tungsten posts 400 that supports the growth of three tissues (strips) in parallel. The opposing side of the culture well contains the vertically mounted force-measuring posts (fiber-optic posts 340) to support the other end of the tissues (see the second objective). On the outsides of the post arrays are graphite sheet-electrodes to supply electrical stimulation across the length of the tissue. Tissue is preferably grown in a triplicate array to provide higher throughput with the system 100.

Objective 2—Ability to Automatically Measure the Passive and Active Contractile Forces of the Tissues within the Incubator, while being Able to Simultaneously Adjust the Length and Tension of the Tissue as Well as the Pacing Frequency The second objective is accomplished through a fiber-optic deflection-force sensing system. A standard, 500 micron diameter plastic optical fiber serves as a stiff but bendable post 340 to which the tissue attaches and bends slightly as it contracts. A position-sensitive photodetector (PSD) 350 beneath the fiber 340 end receives LED light transmitted through the fiber 340 and detects the displacement of the free end of the fiber 340. This photodetector signal is recorded and converted to a displacement and a tissue-generated force based on an equation for a bending cantilever beam. Tissue length is controlled by attaching the other end of the tissue to a rigid tungsten wire (post 400) that is connected to a linear motion module 414, such as an M3-L linear motion module commercially available from NewScale Technologies, Victor, N.Y. (this exemplary module is a piezoelectric linear actuator with absolute position control, 0.5 micron resolution and 6 mm of travel).

Objective 3—Ability to Measure the Action Potentials Generated by the Tissue During the Contractions The third objective is accomplished utilizing an amplifier design published in a 2001 paper by Land, et al entitled "Tools for physiology labs: an inexpensive high-performance amplifier and electrode for extracellular recording" (Land, et al., 2001). The inputs to the amplifier are connected to the tungsten posts 400 that hold the tissue, enabling the extracellular recording of action potentials generated by the tissue strips (grown between the posts 340, 400). Suitable software, such as LabVIEW software, and other equipment, such as a National Instruments data acquisition board (DAQ), can be used for motor control, data collection from all amplifiers, as well as to provide the stimulus pulse to the electrodes.

Objective 4—Ability to Perfuse Media and Testing Agents Easily with the Culture Well (Bath) Using Built-in Fluid Exchange Ports The fourth objective is accomplished with tapped ports in the sides of the culture well 130 near the bottom, into which tubing connectors can be fitted on the sides of the bioreactor system 100. Tubing is routed from the ports to a peristaltic pump to exchange media in the culture well with fresh media (or media containing a soluble biochemical compound or pharmaceutical agent for measuring dose response) at an appropriate rate. Stopcocks are placed in-line with the tubing to allow the tubing to be disconnected without leaking during tissue observation and user interaction with the system.

Advantages of the bioreactor system 100 thus include but are not limited to the following:

a) Length control during non-invasive monitoring of contractile function allows different tissues, or different conditions, to be compared at a consistent baseline length (known in muscle physiology terms as percent of Lmax) to permit an unbiased and standardized comparison of length-dependent contractile force. This is standard practice in muscle physiology experiments, and has been applied to engineered tissues removed from the culture environment for short-term testing. But this damages the tissue, which cannot be returned for subsequent culture and testing. The present system allows for integrated length control and force measurement for long-term testing without disrupting the sterile culture conditions of the engineered tissue. Motorizing the tissue length control allows full force-length testing protocols to be executed repeatedly and non-invasively, and attaching several tissues to the same motor allows economy of the device and higher throughput testing for screening applications. Rows of these motors could be coupled to allow expanded arrays of tissue testing.

b) Using a photodetector to monitor the movement of light transmitted through an optical fiber allows end-post deflection, and thereby contractile force, to be monitored automatically, continuously, and simultaneously in multiple tissues, and obviates the need for video monitoring or video acquisition that limits current systems due to large data storage requirements. The time resolution of the photo signal is also much higher (kilohertz range) than most video camera systems (typically <100 fps) to ensure high fidelity capture of even the most rapid features of the twitch cycle. Our sensing system is also low-cost (a few dollars), compared to alternative video cameras or electronic force sensors (thousands of dollars), which facilitates economical scaling up to multiple tissues in a single bioreactor platform.

c) Because optical visualization of the tissues, for intermittent inspection without removal from the incubator, remains of practical necessity, the bioreactor system is mounted on legs with an angled mirror underneath. Thereby a camera can be placed beside the bioreactor and focused on the mirror, which provides a live image of the engineered tissues.

d) Electrical stimulation electrodes are placed within the culture region to apply field stimulation of the engineered tissues during culture. The electrodes and the motor are electrically synchronized so that the pacing signal and the twitch response are coordinated in time. This is critical for ensuring the stretch signal occurs at the proper time during the muscle twitch. This idea has formed the basis of a clinical technique known as cardiac resynchronization therapy (CRT), in which the timing of electrical impulses is precisely coordinated with phases of the cardiac cycle to maximize pump function of the heart.

e) Because the carbon electrodes are porous, they tend to absorb and accumulate material from the tissue culture well (bath) environment, which compromises their performance and would be detrimental for use in subsequent experiments. Other commercial systems for chronic electrical stimulation of cardiac cells in culture (e.g., c-pace system from Ionoptix) require that their instrumented lid with permanently attached carbon electrodes "need[s] to be cleaned every 24-48 hrs" of use by "soaking in distilled water with a stirrer for a couple of days", which is inconvenient and time consuming, and eventually corrodes the electronic circuit board parts. In the present invention, detachable electrodes use conductive magnets to secure the electrodes in position during use, to easily remove the electrodes for cleaning and quickly replace them with clean electrodes, and to hold the electrodes securely in place when manipulating the bioreactor.

f) To ensure that light is emitted from the end of the fiber-optic, and to make sure the tissue doesn't slip off the end, it is grown at a short distance away from the tip of the fiber-optic end post (and similarly on the tungsten end post at the other end of the tissue). Therefore, a specialized low-adhesion but penetrable tissue casting mold has been developed using a unique combination of Teflon and agarose hydrogel. The Teflon tissue-casting mold is placed at the bottom of the culture well, aligned by tabs that fit into slots on either side of the well. Three dog-bone shaped wells sit under the posts so that the tissue forms around the posts. The ends of the mold are deeper than the length portion of the mold, providing a well that is filled with melted agarose. Once the agarose cools into a firm hydrogel, the posts are pushed through the agarose into the wells. The liquid cell/collagen suspension is pipetted into the wells, and the tissue forms on top of the agarose so that the ends of the post are exposed once the tissue is removed from the casting mold. In addition, PDMS rings (or other types of rings) formed at the ends of the optical fiber may be used to prevent the tissue from slipping off.

g) Exchange of culture media or addition of soluble compounds (e.g. cardiac drugs) for testing typically requires removing a bioreactor system from the incubator every day and carefully using a pipet to replace old media with fresh culture media. To circumvent this cumbersome process and ensure a stable culture environment throughout the lifetime of the tissue, fluid exchange ports are incorporated into the sides of the tissue culture well. By connecting these ports via tubing to a source of culture media and a waste media container, it is straightforward to exchange culture media with minimal disruption of the growing tissues. Valves allow the system to be closed off and disconnected from the fluid containers when necessary. A simple electrical pump can be incorporated to automatically exchange media in the tissue bath (culture well) as desired. By increasing the flow rate, this could also provide mechanical shear stress signals to the tissue, or enhanced transport of oxygen, nutrients and waste materials.

h) The entire system is integrated, controlled, and monitored using custom code written in the LabVIEW programming environment (from National Instruments Corp).

Having described preferred embodiments of the systems and the devices (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims.

What is claimed is:

1. A bioreactor system that is configured to provide length control of engineered tissue and to measure one or more properties of the engineered tissue comprising:
   a housing that includes a culture well;
   at least one first flexible post suspended in the culture well;

at least one second rigid post suspended in the culture well, the second post being spaced from the first post such that the engineered tissue is grown therebetween;

a first device for measuring a contractile force of the engineered tissue, the device including the at least one first post which comprises a fiber-optic that is operatively coupled to a light source and configured to flex when the engineered tissue contracts, the first device further including a sensor for detecting a degree of movement of the at least one first post; and a second device for controlling the length of the engineered tissue, the second device including the at least one rigid second post and an actuator that is operatively coupled to the at least one second post for moving the at least one second post in a controlled manner within the culture well so as to cause a change in a distance between the at least one first post and the at least one second post and thereby control the length of the engineered tissue;

wherein the housing includes a base which contains the culture well and a removable lid with the second device being fixedly attached to the lid;

wherein the fiber-optic passes through the lid with an upper end of the fiber-optic proximate the lid representing a more rigid section of the first post, with a lower section thereof representing a flexible section that flexes in response to applied forces due to tissue contractions.

2. The bioreactor system of claim 1, wherein three or more first posts and three or more second posts are suspended in the culture well for growing three or more engineered tissue specimens.

3. The bioreactor system of claim 2, wherein the three or more first posts are arranged linearly and the three or more second posts are arranged linearly so as to define at least sets of facing posts, each set of posts supporting one engineered tissue specimen resulting in three or more engineered tissue specimens being grown in parallel.

4. The bioreactor system of claim 1, wherein the first device includes a base which is coupled to the housing to position and suspend the at least one first post in the culture well.

5. The bioreactor system of claim 1, wherein the first device includes a fiber optic LED emitter that is coupled to the fiber-optic (first post) for generating a light spot that contacts the sensor which comprises a position-sensitive detector which is configured to measure tissue contractions by measuring the degree of movement of the fiberoptic by measuring a position of the light spot.

6. The bioreactor system of claim 5, wherein a floor of the culture well is formed of a material that allows passage of light from the fiber-optic to the position-sensitive detector which is disposed below the culture well.

7. The bioreactor system of claim 1, wherein the fiber-optic has a diameter of about 0.55 mm.

8. The bioreactor system of claim 1, wherein the second post comprises a rigid tungsten post.

9. The bioreactor system of claim 1, wherein the actuator comprises a linear actuator that is operatively coupled to a post holder to which the at least one second post is coupled.

10. The bioreactor system of claim 9, wherein the post holder is operatively coupled to linear slides that under actuation of the linear actuator results in linear movement of the post holder which results in linear movement of the engineered tissue due to one end of the engineered tissue being coupled to the second post.

11. The bioreactor system of claim 1, further including a pair of electrodes disposed within the culture well outside of the at least one first post and the at least one second post for supplying electrical stimulation across a length of the engineered tissue.

12. The bioreactor system of claim 11, wherein the electrodes comprise graphite sheet electrodes arranged in the culture well such that the at least one first post and the at least one second post are disposed therebetween.

13. The bioreactor system of claim 1, wherein each of the first and second devices is operatively coupled to a controller for controlling operation and functionality thereof.

14. The bioreactor system of claim 1, further including a mechanism for measuring action potentials generated by the engineered tissue during contractions.

15. The bioreactor system of claim 14, wherein the mechanism includes an amplifier that is configured such that inputs thereof are connected to the at least one second post enabling extracellular recording of action potentials generated by the engineered tissue.

16. The bioreactor system of claim 1, wherein the culture well includes built-in fluid exchange ports that allow for the perfusion of media and testing agents into and out of the culture well.

17. The bioreactor system of claim 1, further including a pair of stimulating electrodes that are detachably attached to the lid and positioned in the culture well such that the at least one first post and the at least one second post are disposed between the electrodes.

18. The bioreactor system of claim 17, wherein the electrodes include conductive magnets for fixedly, yet detachably, attaching the electrodes to the lid such that the electrodes are maintained in fixed positions during use, are easily removable from the lid for cleaning and are quickly replaceable after cleaning thereof.

* * * * *